(12) United States Patent
Tang et al.

(10) Patent No.: US 8,175,712 B2
(45) Date of Patent: May 8, 2012

(54) HOMOTOPIC CONDITIONING OF THE BRAIN STEM BAROREFLEX OF A SUBJECT

(75) Inventors: Xiaorui Tang, Hershey, PA (US); Barry R. Dworkin, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 1200 days.

(21) Appl. No.: 11/850,251

(22) Filed: Sep. 5, 2007

(65) Prior Publication Data
US 2008/0058890 A1      Mar. 6, 2008

Related U.S. Application Data

(60) Provisional application No. 60/824,519, filed on Sep. 5, 2006, provisional application No. 60/828,475, filed on Oct. 6, 2006.

(51) Int. Cl.
*A61N 1/00* (2006.01)
(52) U.S. Cl. .......................................... 607/44
(58) Field of Classification Search ...................... 607/44
See application file for complete search history.

(56) References Cited

U.S. PATENT DOCUMENTS

| | | | |
|---|---|---|---|
| 5,199,428 A | 4/1993 | Obel et al. | |
| 5,707,400 A | 1/1998 | Terry, Jr. et al. | |
| 5,727,558 A | 3/1998 | Hakki et al. | |
| 6,050,952 A | 4/2000 | Hakki et al. | |
| 6,178,352 B1 | 1/2001 | Gruzdowich et al. | |
| 6,393,324 B2 | 5/2002 | Gruzdowich et al. | |
| 6,522,926 B1 | 2/2003 | Kieval et al. | |
| 6,658,298 B2 | 12/2003 | Gruzdowich et al. | |
| 6,681,136 B2 | 1/2004 | Schuler et al. | |
| 6,850,801 B2 | 2/2005 | Kieval et al. | |
| 6,957,106 B2 | 10/2005 | Schuler et al. | |
| 6,985,774 B2 | 1/2006 | Kieval et al. | |
| 7,194,313 B2 * | 3/2007 | Libbus .......................... 607/42 |
| 2003/0060857 A1 | 3/2003 | Perrson et al. | |
| 2004/0102818 A1 | 5/2004 | Hakky et al. | |
| 2005/0149143 A1 | 7/2005 | Libbus et al. | |

(Continued)

OTHER PUBLICATIONS

V. Burt, P. Whelton, E. Roccella, C. Brown, J. Cutler, M. Higgins, M. Horan, D. Labarthe; "Prevalence of Hypertension in the U.S. Adult Population," Hypertension, 1995; 25:305-313.

(Continued)

*Primary Examiner* — Eric D. Bertram
*Assistant Examiner* — Elizabeth K So
(74) *Attorney, Agent, or Firm* — Gifford, Krass, Sprinkle, Anderson & Citkowski, P.C.

(57) ABSTRACT

Disclosed are methods for regulating blood pressure in a subject which include administering a first induction stimulus effective to sensitize brainstem baroreflex neurons of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration. An induction stimulus has diminished effectiveness to sensitize neurons in the nucleus tractus solitarius of the subject in the presence of an NMDA receptor antagonist. One or more additional induction stimuli are optionally administered to regulate blood pressure in the subject.

19 Claims, 5 Drawing Sheets

U.S. PATENT DOCUMENTS

| | | |
|---|---|---|
| 2005/0214338 A1* | 9/2005 | Guitton et al. ............... 424/423 |
| 2005/0222640 A1 | 10/2005 | Schwartz et al. |
| 2006/0041283 A1 | 2/2006 | Gelfand et al. |
| 2006/0102171 A1* | 5/2006 | Gavish ........................ 128/95.1 |

OTHER PUBLICATIONS

Schwartz, L. Griffith, A. Neistadt, N. Hagfors; "Chronic Carotid Sinus Nerve Stimulation in the Treatment of Essential Hypertension," American Journal of Surgery, vol. 114, Jul. 1967, pp. 5-15.

T. Lohmeier; "The Sympathetic Nervous System and Long-Term Blood Pressure Regulation," American Journal of Hypertension, 2001; 14: 147-154.

T. Lohmeier, S. Warren, J. Cunningham; "Sustained Activation of the Central Baroreceptor Pathway in Obesity Hypertension," Hypertension, 2003; 42(1):96-102.

T. Lohmeier, T. Dwyer, D. Hildebrandt, E. Irwin, M. Rossing, D. Serdar, R. Kieval; "Influence of Prolonged Baroreflex Activation on Arterial Pressure in Angiotensin Hypertension," Hypertension, 2005; 46(5): 1194-200.

T. Lohmeier, J. Lohmeier, S. Warren, P. May, J. Cunningham; "Sustained Activation of the Central Baroreceptor Pathway in Angiotensin Hypertension," Hypertension, Feb. 2002, pp. 550-556.

X. Tang, B. Dworkin; "Long-Term Potentiation (LTP) of the Aortic Baroreceptor input to the NTS," Society of Neuroscience, 2005.

B. Dworkin; "Models of Dynamic Regulation," Learning and Physiological Regulation, pp. 49-84.

B. Dworkin, S. Dworkin, X. Tang; "Carotid and aortic bioreflexes of the rat: I. Open-loop steady-state properties and blood pressure variability," Am J Physiol Regulatory Integrative Comp Physiol, 279: R1910-1921, 2000.

X. Tang, B. Dworkin; "Baroreflexes of the rat. V. Tetanus-induced potentiation of ADN A-fiber responses at the NTS," Am J Physiol Regul Integr Comp Physiol 293: R2254-2259, 2007.

X. Tang, B. Dworkin; "Baroreflexes of the rat. IV. ADN-evoked responses at the NTS," Am J Physiol Regul Integr Comp Physiol 293: R2243-2253, 2007.

B. Dworkin; "Interoception," Handbook of Psychophysiology, Third Edition, pp. 482-506.

I. Hajjar, T. Kotchen; "Trends in Prevalence, Awareness, Treatment and Control of Hypertension in the United States, 1988-2000," JAMA Jul. 9, 2003, vol. 290, No. 2, pp. 199-206.

A. Cowley, Jr.; "Long-term control of arterial blood pressure," Physiol Review, 1992; 72: 231-300.

T. Lohmeier, E. Irwin, M. Rossing, D. Serdar, R. Kieval; "Prolonged Activation of the Baroreflex Produces Sustained Hypotension," Hypertension, 2004, 43(2): 306-11.

J. McCubbin, J. Green, I. Page; "Baroreceptor Function in Chronic Renal Hypertension," Circ. Res. 1956, 4: 205-210.

A. Soukas; "Overall Systems Analysis of the Carotid Sinus Baroreceptor Reflex Control of the Circulation," Anesthsiology, 79:1402-12, Dec. 1993.

S. Schwartz; "Clinical Applications of Carotid Sinus Nerve Stimulation," Cardiovascular Therapy, 1969, 1: 208-222.

M. Mohaupt, H. Savolainen, C. Cain, F. Frey, T. Carrel, J. Schmidli; "Chronic Electrical Activation of the Carotid Sinus Baroreflex by Implanted Electrodes for Blood Pressure Reduction in Man: First Experience in a Hypertensive Patient," Kidney Blood Pressure Research, 2004, 27: 299.

J. Schmidli, h. Savolainen, E. Irwin, T. Peters, C. Cain, R. Martin, F. Eckstein, T. Carrel; "A Completely New Treatment for Hypertension?," Journal of Hypertension, 2004, 22 (Supplement 2); S252.

J. Schmidli, M. Mohaupt, H. Savolainen, Y. Allemann, E. Irwin, T. Peters, R. Martin, R. Kieval, T. Carrel; "Response to Acute Electrical Activation of the Carotid Baroreflex is Maintained in Drug Refractory Hypertension," Journal of Hypertension, 2005, 23 (Supplement 2): S6.

* cited by examiner

HOMOTOPIC CONDITIONING OF THE BRAIN STEM BAROREFLEX OF A SUBJECT

REFERENCE TO RELATED APPLICATIONS

This application claims priority of U.S. Provisional Patent Application Ser. No. 60/824,519 filed Sep. 5, 2006 and U.S. Provisional Patent Application Ser. No. 60/828,475 filed Oct. 6, 2006, the entire content of both of which is incorporated herein by reference.

GOVERNMENT SPONSORSHIP

This invention was made with govnerment support under Grant No. R01 HL40837, awarded by The National Institutes of Health/NHLB. The Government has certain rights in the invention.

FIELD OF THE INVENTION

The present invention relates generally to blood pressure regulation. In particular, methods according to embodiments of the present invention relate to homotopic conditioning of neurons in the brainstem of a subject for regulation of blood pressure.

BACKGROUND OF THE INVENTION

There are many factors that affect blood pressure, including volume and salt content of body water, condition of the kidneys, nervous system, blood vessels, and various hormone levels. Baroreflexes are the major mechanism of blood pressure stabilization. One of the key observations in the reflex control of the circulation is that stimulation of the baroreflex pressure sensors, the baroreceptors, decreases blood pressure (Shoukas A A. Overall systems analysis of the carotid sinus baroreceptor reflex control of the circulation. Anesthesiology 79: 1402-1412, 1993). The major baroreceptors are located in the carotid sinus and the aortic arch; electrical stimulation of nerves from these areas is interpreted by the brain as an increase of blood pressure, and the brain activates compensatory (negative feedback) mechanisms, which, by increasing parasympathetic, and decreasing sympathetic activity, reduce blood pressure.

Since the mid 1960's, electrical stimulation of the carotid sinus nerve has been used to treat severe hypertension patients, who were resistant to medications (Schwartz S I, Griffith L S C, Neistadt A, et al.: Chronic carotid sinus nerve stimulation in the treatment of essential hypertension. Am J Surg 1967, 114: 5-15); (Schwartz S I: Clinical applications of carotid sinus nerve stimulation. Cardiovasc Clinl 1969, 1: 208-222). In these early studies, electrodes were attached directly to the carotid sinus nerve, and an implanted stimulator was used to continuously supply current pulses to the electrodes. Results from these early studies were promising, and suggested the possibility that prolonged baroreceptor nerve stimulation could generate sustained reductions in arterial pressure in hypertension patients. However, the baroreflex stimulation technologies have never become established; and these early efforts have never become clinically practical. One of the main factors that discouraged the establishment of the baroreflex stimulation technology was the dominance of the baroreflex resetting theory. In these early studies, continuous stimulation was used to produce sustained reductions in blood pressure. This strategy was logical from a conventional linear time invariant (LTI) control theory perspective; however, whether the baroreflex is, indeed, a "conventional" control system, was and still is, open to question. In fact, in the mid 50's, McCubbin et al. (McCubbin J W, Green J H, Page I H. Baroreceptor function in chronic renal hypertension. Circ Res. 1957; 4; 205-210) demonstrated a marked resetting of the arterial baroreflex in chronic hypertension, and since then there has been doubt, in cardiovascular medicine, as to whether the baroreflexes actually do participate in long-term control of arterial pressure (Cowley, A. W. Jr. Long-term control of the arterial blood pressure. Physiol Rev. 1992; 72: 231-300); (Lohmeier, T. E. The sympathetic nervous system and long-term blood pressure regulation. Am J Hypertens. 2001; 14: 147s-154s).

Irrespective of theoretical considerations, hypertension, or high blood pressure, remains among the most serious diseases contributing to morbidity and mortality in the US. Sustained hypertension can cause heart failure, stroke, kidney disease, and damage to many organs. Data from the National Health and Nutrition Examination Survey (NHANES) indicated that 50 million or more Americans suffer from high blood pressure (Burt V L, Whelton P, Roccella E J, Brown C, Cutler J A, Higgins M, et al. Prevalence of hypertension in the US adult population. Results from the Third National Health and Nutrition Examination Survey, 1988-1991. Hypertension 1995; 25; 305-13); (Hajjar I, Kotchen T A. Trends in prevalence, awareness, treatment, and control of hypertension in the United States, 1988-2000. JAMA 2003; 290: 199-206); estimates from the Seventh Report of the Joint National Committee on the Prevention, Detection, Evaluation, and Treatment of High Blood Pressure (JNC7), indicated that only 34% of the hypertensive population in the US is adequately controlled (Chobian A V, Bakris G L, Black H R, et al.: Seventh report of the Joint National Committee on Prevention, Detection, Evaluation, and Treatment of high blood pressure. Hypertension 2005, 42: 1026-1252). Among all patients with hypertension, at least 10% suffer from resistant hypertension, which is defined as failure to achieve a blood pressure of less than 150/90 mmHg, despite the use of a rational triple-drug regimen in optimal doses. Given such a high rate of pharmacologically intractable hypertension, it is clear that alternative treatment technologies are needed.

Thus, new methods are required for regulating blood pressure in individuals having hypertension or other blood pressure-related pathologies.

SUMMARY OF THE INVENTION

A method for regulating blood pressure in a subject is provided according to embodiments of the present invention which includes administering a first induction stimulus effective to sensitize neurons in the brainstem of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration. An induction stimulus has diminished effectiveness to sensitize neurons in the brainstem of the subject when an NMDA receptor antagonist is administered to the brainstem neurons simultaneously with the induction stimulus or immediately before the induction stimulus.

In particular embodiments, the sensitized neurons are NTS neurons. In further embodiments, the sensitized neurons are caudal ventrolateral neurons (CVL) of the brainstem.

Embodiments of methods of the present invention include administration of one or more additional induction stimuli effective to sensitize neurons in the nucleus tractus solitarius of a subject at about 10-15 hour intervals following administration of the first induction stimulus.

First and additional induction stimuli modalities include electrical, chemical, mechanical, thermal and/or biological agent stimuli. A first induction stimulus may be the same or different modality as the one or more later delivered stimuli.

In particular embodiments of methods of the present invention, an induction stimulus is a tetanic electrical stimulus delivered to a component of an endogenous biological blood pressure regulatory system of the subject. In particular embodiments, an induction stimulus is a tetanic electrical stimulus delivered to a baroreceptor afferent nerve and stimulates C fibers, or higher threshold fibers, of the baroreceptor afferent nerve to sensitize neurons in the nucleus tractus solitarius of a subject. In further specific embodiments of a method of the present invention, an induction stimulus is delivered to an aortic depressor nerve and/or a carotid sinus nerve of the subject.

A stimulus is administered by a stimulation device external to the body of the subject, at least partially implanted in the body of the subject or by a stimulation device completely implanted in the body of the subject.

An exemplary biological agent administered as an induction stimulus is an NMDA receptor agonist and/or a partial NMDA receptor agonist. In particular embodiments of a method of the present invention, an induction stimulus is a dose of an NMDA receptor agonist and/or partial NMDA receptor agonist delivered to the nucleus tractus solitarius of the subject.

In general, an induction stimulus is effective to decrease variability in blood pressure in the subject for a duration in the range of about 10-15 hours following the induction stimulus. In particular embodiments of the present invention, variability in blood pressure in the subject is decreased by about 5-50% for about 10-15 hours following an induction stimulus.

Methods for regulating blood pressure in a subject according to embodiments of the present invention include administering an induction stimulus which is a tetanic electrical stimulus effective to sensitize neurons in the nucleus tractus solitarius of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration. The induction stimulus has diminished effectiveness to sensitize neurons in the nucleus tractus solitarius of the subject when an NMDA receptor antagonist is administered to the NTS neurons simultaneously with the induction stimulus or immediately before the induction stimulus. Also disclosed are methods including administering one or more additional induction stimuli in the form of tetanic electrical stimuli effective to sensitize neurons in the nucleus tractus solitarius of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration.

Further embodiments of methods of regulating blood pressure according to the present invention include a) selecting stimulus parameters for administering a tetanic electrical stimulus to high threshold C-fibers of baroreceptor afferents, the stimulus parameters comprising a frequency in the range of about 50-150 Hz; a high current pulse intensity in the range of about 50-600 microAmps; a pulse duration in the range of about 100-500 microseconds; a train duration in the range of about 1-5 s, a train frequency in the range of about 1 train/10-20 s; and a train number in the range of about 5-20 trains; b) stimulating low threshold A-fibers of baroreceptor afferents in a subject, the stimulating comprising administering a stimulus pulse train of low current intensity characterized by stimulus parameters comprising a frequency in the range of about 15-60 Hz; current pulse intensity in the range of about 5-50 microAmps; a pulse duration in the range of about 100-500 microseconds; and a stimulation duration in the range of about 10-60 seconds; c) measuring evolked blood pressure (EBP) response in the subject to the stimulating low threshold A-fibers of baroreceptor afferents to determine a first average EBP response value; d) stimulating high threshold C-fibers of baroreceptor afferents using the stimulus parameters selected in a); e) measuring EBP response to the stimulating low threshold A-fibers of baroreceptor afferents to determine a second average EBP response value; f) comparing the first average EBP response value and the second average EBP response value, wherein successful induction of an enhanced baroreflex is indicated by the second average EBP response value greater than the first average EBP response value; g) repeating a)-f) until the second average EBP response value is greater than the first average EBP response value, indicative that selected stimulus parameters successfully inducing an enhanced baroreflex; and h) administering one or more additional induction stimuli characterized by the selected stimulus parameters successful induction of an enhanced baroreflex at about 10-15 hour intervals.

DETAILED DESCRIPTION OF THE PREFERRED EMBODIMENTS

Classical conditioning paradigms involve learning an association of a stimulus and response which are not usually associated. For example, a stimulus such as presentation of food to a dog produces a reflexive salivation response and classical conditioning teaches the dog to associate a new stimulus, such as the sound of a bell, with the appearance of food such that the new stimulus is associated with the reflexive response. Subsequent to the conditioning, the new stimulus produces the reflexive response even in the absence of the original stimulus. This classical conditioning is heterotopic, that is, the original stimulus and the new stimulus are presented in different sensory modalities. Homotopic conditioning refers to conditioning in which the original stimulus and new stimulus are presented in the same sensory modality.

Methods are provided according to embodiments of the present invention which produce homotopic conditioning of the endogenous blood pressure regulatory system of an individual subject in order to regulate blood pressure in the subject.

Components of the endogenous blood pressure regulatory system, such as baroreceptors, afferent nerve fibers, nucleus tractus solitarius neurons, caudal ventrolateral medullar neurons and efferent nerve fibers for example. Baroreceptors are stretch sensors located in walls of large arteries, particularly in the aortic arch and carotid sinus. Baroreceptor afferents are sensory nerve fibers which transmit signals from baroreceptors to neurons in the cardiovascular center of the NTS. Baroreceptor afferents from baroreceptors located in the aortic arch and carotid sinus form the aortic depressor nerve (ADN) and carotid sinus nerve (CSN), respectively.

The ADN and CSN are functionally equivalent. Both the ADN and the CSN contain two electrophysiologically distinct fiber types, myelinated A-fibers which are large diameter, fast conducting, and lower pressure activated fibers, and non-myelinated C-fibers which are small diameter, slower conducting, and higher pressure activated fibers.

The ADN and CSN join with other nerve fibers to form the vagus (cranial nerve X) and glossopharyngeal (cranial nerve IX) nerves, respectively.

Brainstem baroreflex neurons which mediate the baroreflex in a subject include neurons innervated by baroreceptor afferents, such as NTS neurons, as well as central relay neurons such as caudal ventrolateral (CVL) neurons of the medulla.

Details of baroreceptor reflexes and anatomy are further described in Persson, P. B. and Kirchheim, H. R., Eds., Baroreceptor Reflexes: Integrative Functions and Clinical Aspects, Springer, 1991.

In a healthy subject, the endogenous blood pressure regulatory system responds to a rise in blood pressure by producing a depressor response. The term "depressor response" refers to a reflex response which includes a decrease in blood pressure mediated by relaxation of vascular muscle.

Figure 1:
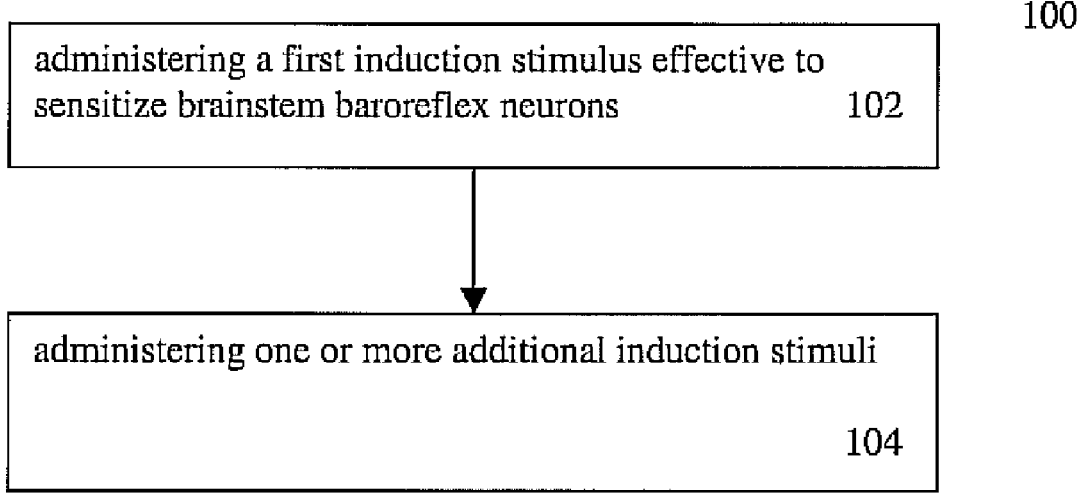
FIG. 1 is a block diagram illustrating a method of regulating blood pressure according to embodiments of the present invention.

As illustrated diagrammatically in FIG. 1, a method 100 for regulating blood pressure in a subject is provided according to embodiments of the present invention which includes 102 administering a first induction stimulus. The induction stimulus is effective to sensitize brainstem baroreflex neurons of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration. As further shown in FIG. 1, embodiments of methods of the present invention 100 include 104 administration of one or more additional induction stimuli effective to sensitize brainstem baroreflex neurons of a subject at about 10-15 hour intervals following administration of the first induction stimulus.

An induction stimulus has diminished effectiveness to sensitize neurons in the nucleus tractus solitarius of the subject when an HNMA receptor antagonist is administered to the NTS neurons simultaneously with the induction stimulus or immediately before the induction stimulus.

The term "sensitize" refers to administering an induction stimulus to brainstem baroreflex neurons of the subject such that a second, weaker stimulus to a baroreceptor, baroreceptor afferent, NJS neuron and/or CVL neuron triggers a depressor response where the weaker stimulus would not have triggered the depressor response prior to the administration of the first induction stimulus and/or a second, weaker stimulus triggers a larger depressor response than it would have triggered prior to the administration of the first induction stimulus. The second, weaker stimulus may be an exogenously administered test stimulus, administered to demonstrate sensitization of the neurons by the administration of the first induction stimulus. In operation as a method of regulation of blood pressure in particular embodiments, the second, weaker stimulus is a rise in blood pressure in the subject.

The term "subject" refers to a mammal, including primates, and particularly to a human.

In particular embodiments of a method of the present invention, one or more additional induction stimuli are administered following a first administration of an induction stimulus. For example, a second induction stimulus is administered when neurons in the nucleus tractus solitarius sensitized by a first induction stimulus become desensitized, that is, when the neurons no longer respond to the weaker stimulus to trigger a depressor response, or the depressor response to the weaker stimulus decreases to the level prior to the first induction stimulus. Desensitization of neurons in the nucleus tractus solitarius is typically determined by a rise in blood pressure, typically 10-15 hours after the first induction stimulus, symptomatic of neurons in the nucleus tractus solitarius no longer or decreased responding to a weak stimulus to trigger a depressor response.

Administration of an induction stimulus decreases variability in blood pressure over a period of time following the induction stimulus. The term "blood pressure variability" refers to the variation of the systolic (sBP), diastolic (dBP) or mean arterial pressure (MAP) around the average values of the sBP, dBP and MAP, respectively, over a period of minutes to days. Blood pressure variability can be measured by standard deviation (SD), variance, and coefficient of variation (CV), defined as the standard deviation divided by the mean, multiplied by 100%, of the sBP, dBP and MAP of the measuring period. The baroreflex controlled blood pressure variability can also be measured by the very low frequency (0.01-0.2 Hz) power of sBP spectrum of the measuring period.

In general, an induction stimulus is effective to decrease variability in blood pressure in the subject while NTS neurons are sensitized, a period of time in the range of about 10-15 hours following the induction stimulus. In particular embodiments of the present invention, variability in blood pressure in the subject is decreased by about 5-50% for about 10-15 hours following the induction stimulus.

Figure 2:
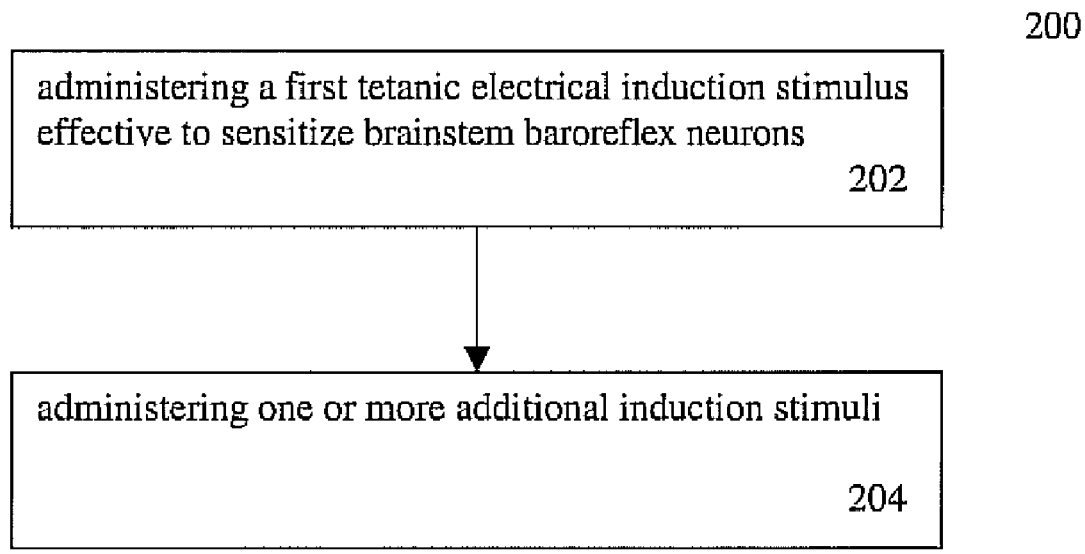
FIG. 2 is a block diagram illustrating a method of regulating blood pressure according to embodiments of the present invention.

Particular methods for regulating blood pressure in a subject according to embodiments of the present invention 200 are illustrated diagrammatically in FIG. 2 and include 202 administering an induction stimulus which is a tetanic electrical stimulus effective to sensitize brainstem baroreflex neurons of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration. Also disclosed are methods including 204 administering one or more additional tetanic electrical stimuli effective to sensitize brainstem baroreflex neurons of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration.

The present invention demonstrates that following a brief high current "tetanic" stimulation of baroreceptor afferents which are C-fibers, baroreceptor afferent A fiber evoked responses at the brainstem baroreflex neurons, such as the dorsomedial solitary nucleus (dmNTS), the first relay station of the baroreflexes in the brain, are increased for hours. Thus, a long-term potentiation (LTP) is elicited at the dmNTS by the brief tetanic stimulation of a baroreceptor afferent, such as the ADN and/or CSN. This demonstrates that sensitivity of the NTS to A-fiber baroreceptor afferents is regulated by activation of C fiber baroreceptor afferents, such that after a few seconds of tetanic stimulation sufficient to stimulate C fiber baroreceptor afferents, small blood pressure increases trigger larger depressor responses than before the tetanic stimulation, and thus ameliorate hypertension for 10-15 hours.

Figure 3:
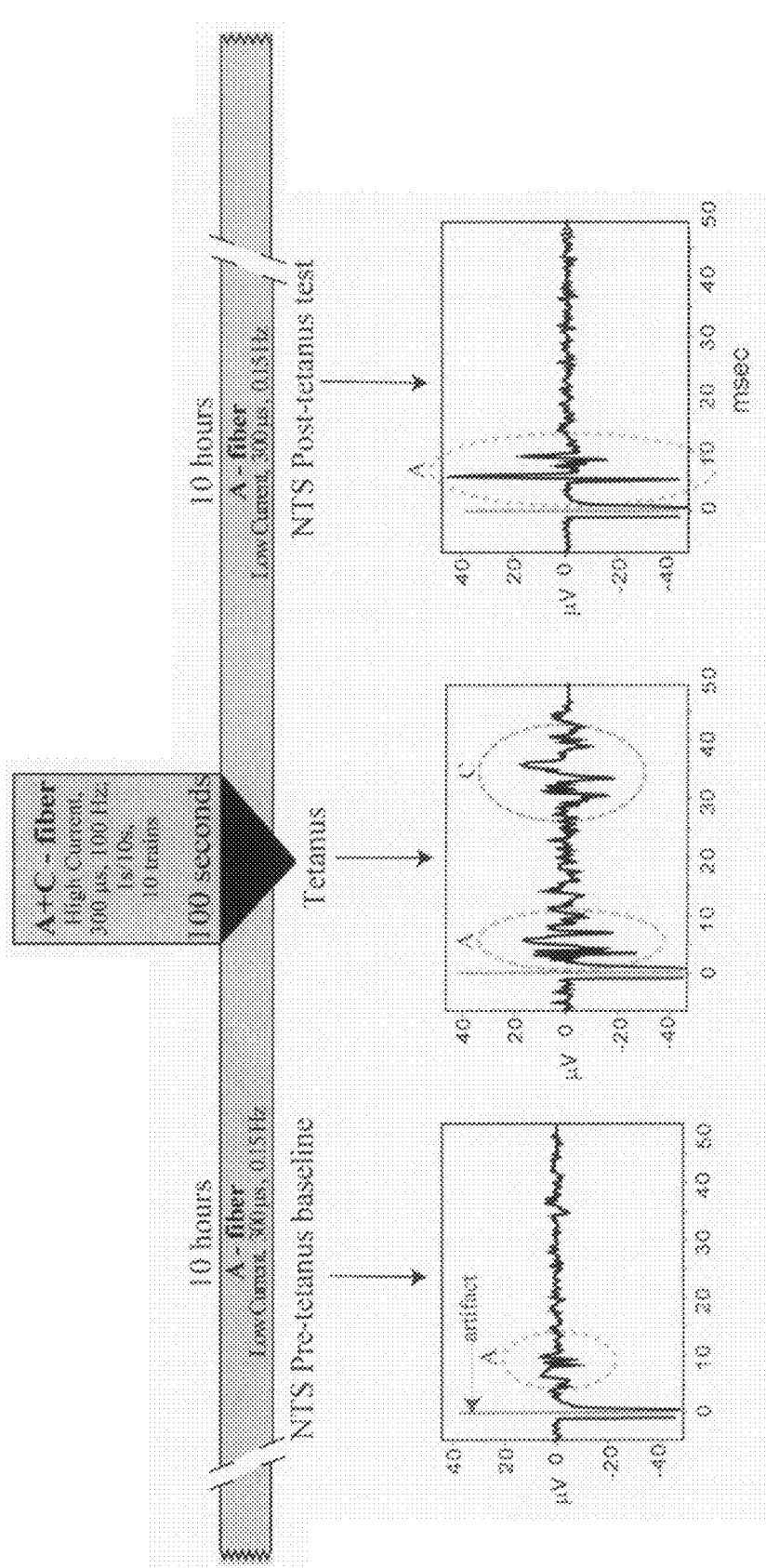
FIG. 3 is an image illustrating traces of recorded nucleus tractus solitarius neurons before, during and after administration of an induction stimulus.

This is illustrated in FIG. 3 showing the pre-induction stimulus (pre-LTP) response of NTS neurons to a "test" stimulus sufficient to activate an A-fiber baroreceptor afferent in a rat. The particular "test" stimulus strength shown is a low current, 300 microsecond, 0.15 Hz stimulus. A tetanic electrical stimulation sufficient to activate C-fiber baroreceptor afferents is administered. The particular induction stimulus administered is a high current, 300 microsecond, 100 Hz stimulus administered at is/10 s, 10 trains.

The results presented in FIG. 3 illustrate three phases in the experimental protocol used to demonstrate induction of baroreflex neuron sensitization, a pre-tetanus baseline phase, indicated at the left of the figure, a tetanus phase, indicated at center of the figure, and a post-tetanus test, indicated at right. The three traces in the figure are the averaged NTS evoked responses for a typical hour during each experimental phase. Circles in the traces demonstrate the shapes and locations of the A- and C-fiber evoked response components. During the pre-tetanus baseline phase a "low current" stimulation is administered such that only A-fibers were activated, pseudo-random inter-pulse interval=6±1 s, pw=300 μs. This phase continued until the evoked responses (ER) of the neurons was stable for 10 consecutive hours. During the tetanus phase, a current with sufficient strength to activate both A and C-fibers was applied; this tetanic induction stimulation was 1000 "high current" pulses, 10 trains (PW=300 μs, 100 Hz, train=1 s), inter-train interval=9 s, which were delivered over 100 seconds. Following the induction stimulation, the post-tetanic test phase is identical to the baseline phase, i.e. only A-fibers were activated for 10 consecutive hours. The A-fiber "low current" was established by an explicit transduction curve analysis, as that, which elicited maximal A-fiber and no or minimal C-fiber ERs.

It is appreciated that when C-fiber baroreceptor afferents are activated, the stimulus is also sufficient to activate A-fiber baroreceptor afferents. In this case, demonstration that the induction stimulus is effective to sensitize NTS neurons is shown by administration of a second test stimulus. The second test stimulus is identical to the original test stimulus and is administered after the induction stimulus. An enhanced response by NTIS neurons to the second test stimulus is observed, indicating that the NTS neurons are sensitized.

Induction Stimulus

An induction stimulus administered to a subject according to embodiments of the present invention is a stimulus which sensitizes brainstem baroreflex neurons of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration.

First and additional induction stimuli modalities include electrical, chemical, mechanical, thermal and/or biological agent stimuli. A first induction stimulus may be the same or different modality as the one or more later delivered induction stimuli.

In particular embodiments of methods of the present invention, the first induction stimulus is a tetanic electrical stimulus. In specific embodiments, a tetanic electrical induction stimulus is administered which stimulates C fibers of the aortic depressor nerve and/or the carotid sinus nerve to sensitize brainstem baroreflex neurons of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration.

A tetanic electrical induction stimulus is a series of pulse trains of high current intensity effective to stimulate C-fibers of baroreceptor afferents. Typical parameters for a tetanic electrical induction stimulus include a frequency in the range of about 50-150 Hz; a high current pulse intensity in the range of about 50-600 microAmps; a pulse duration in the range of about 100-500 microseconds; a train duration in the range of about 1-5 s, a train frequency in the range of about 1 train/10-20 s; and a train number in the range of about 5-20 trains;

In contrast, a "test" electrical stimulus is a series of pulse trains of low current intensity stimulus effective to stimulate low threshold A-fibers of baroreceptor afferents and ineffective to stimulate the majority of higher threshold C-fibers of baroreceptor afferents. Typical parameters for a test electrical stimulus of low current intensity are a frequency in the range of about 15-60 Hz; a current pulse intensity in the range of about 5-50 microAmps; a pulse duration in the range of about 100-500 microseconds; and a stimulation duration in the range of about 10-60 seconds;

The tetanic electrical stimulus is delivered to a component of an endogenous biological blood pressure regulatory system of a subject. In particular embodiments, an induction stimulus is a tetanic electrical stimulus delivered to a baroreceptor afferent of the subject such as the aortic depressor nerve and/or carotid sinus nerve of the subject.

Exemplary chemical and biological agents include depolarizing agents and receptor ligands.

A particular biological agent administered as an induction stimulus is an NMDA receptor agonist and/or partial agonist. In particular embodiments of a method of the present invention, an induction stimulus is a dose of an NMDA receptor agonist delivered to the nucleus tractus solitarius of the subject.

Optionally, two or more induction stimuli of differing stimulation modalities may be administered. Thus, for example, an electrical stimulation and a biological agent stimulus are administered, together or at different times, in particular embodiments of methods of the present invention.

In one embodiment, an NMDA receptor agonist and/or NMDA receptor partial agonist is administered to a subject as an induction stimulus, either alone or in conjunction with another type of induction stimulus. NMDA receptor agonists illustratively include NMDA and homoquinolinic acid. NMDA partial agonists include D-cycloserine and 1-aminocyclopropanecarboxylic acid (ACPC).

Induction Stimulus Administration

An induction stimulus administered to a subject is delivered by a stimulation device operable to deliver an electrical, chemical, mechanical, thermal and/or biological agent stimulus effective to sensitize neurons in the brain stem which mediate the baroreflex in a subject.

Neurons in the brain stem which mediate the baroreflex in a subject include neurons innervated by baroreceptor afferents, such as NTS neurons, as well as central relay neurons such as caudal ventrolateral (CVL) neurons of the medulla.

In a particular embodiment, an induction stimulus is administered which is effective to sensitize neurons in the nucleus tractus solitarius of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration.

In a further embodiment, an induction stimulus is administered which is effective to sensitize neurons in the CVL of a subject for a period of time in the range of about 10-15 hours thereby producing an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration.

A stimulation device optionally includes control circuitry, such as an activation control. In operation, activation of a stimulator device is achieved by manual activation, remote activation and/or by automated activation, such as by programming a programmable component of the device to administer a stimulus and/or monitor a physiological parameter, such as blood pressure, in the subject.

A stimulation device optionally includes programmable memory for storing data including operation parameters such as time of administration of a stimulus as well as duration and strength of a stimulus.

A sensor is optionally used to monitor blood pressure or other physiological parameter in a subject. Blood pressure or another physiological parameter may be monitored continuously, periodically or episodically. Optionally, a sensor is in data communication with the stimulation device. For example, a blood pressure sensor is in data communication with the stimulation device such that a particular blood pressure value triggers administration of an induction stimulus.

A stimulation device may be powered by any type of power source, illustratively including a battery and/or capacitor. In one option, a stimulation device is powered remotely, such as by radio frequency coupling or other electromagnetic coupling.

An induction stimulus is administered by a stimulation device external to the body of the subject, at least partially implanted in the body of the subject or by a stimulation device completely implanted in the body of the subject.

Administration of one or more electrical induction stimuli is accomplished using an electrical stimulation device including a stimulus generator coupled to at least one electrode. For example, the stimulus generator and at least one electrode are coupled by at least one electrical lead extending between the generator and the at least one electrode.

In particular embodiments an electrical stimulation device is positioned such that the stimulus generator is external to the body of the subject and the at least one electrode is internal to the body of the subject. In further embodiments, both the stimulus generator and the one or more electrodes are implanted in the body of the subject. Implantation and partial implantation of a stimulator device and positioning of components so as to deliver a stimulus to a target site is known in the art and requires no undue experimentation.

In further embodiments of the present invention, both the stimulus generator and the one or more electrodes are external to the body of the subject. The specific location of the stimulus generator and the one or more electrodes varies depending on factors including the physical characteristics of the subject to be treated illustratively including the size, age, weight and general health of the subject.

In certain embodiments, the electrode or electrodes are positioned sufficiently in proximity to a baroreceptor afferent, such as a carotid sinus nerve and/or an aortic depressor nerve, that an electrical stimulus from the electrode or electrodes stimulates the baroreceptor afferent. For example, the electrode or electrodes are in electrical communication with a carotid sinus nerve and/or an aortic depressor nerve of the subject and are optionally positioned to contact one or both nerves.

In further embodiments, an electrode or electrodes are positioned on the carotid sinus and aortic arch, such that an electrical stimulus from the electrode(s) stimulate the baroreceptors of the subject.

Typically, an induction stimulus sensitizes the blood pressure regulatory system for a period of time in the range of about 10-15 hours. Thus, a repeat of an induction stimulus is optionally administered as necessary to re-sensitize the brainstem baroreflex neurons or to maintain the brainstem baroreflex neurons in a sensitized state.

In further embodiments, a stimulation device is configured to deliver a chemical, mechanical, thermal and/or biological agent induction stimulus. For example, a chemical or biological agent is delivered by an implanted or external pump configured to deliver an amount of the chemical or biological agent effective to sensitize brainstem baroreflex neurons of a subject for a period of time in the range of about 10-15 hours thereby producing an enhanced baroreflex in the subject, wherein the enhanced baroreflex is characterized in that a threshold blood pressure for generating a depressor response is lower than prior to chemical or biological agent induction stimulus administration, the depressor response in the subject is larger than prior to chemical or biological agent induction stimulus administration or both the threshold blood pressure for generating a depressor response is lower than prior to chemical or biological agent induction stimulus administration and the depressor response in the subject is larger than prior to chemical or biological agent induction stimulus administration.

A chemical or biological agent delivery device such as a pump may include a reservoir for the chemical or biological agent and a conduit from the reservoir to an outlet. The outlet is positioned proximal to a target site in the subject's body. A target site for a chemical or biological agent is a site stimulated by the chemical or biological agent effective to sensitize brainstem baroreflex neurons of the subject. Exemplary target sites include the nucleus tractus solitarius, baroreceptors, baroreceptor afferents, and central relay neurons such as caudal ventrolateral (CVL) neurons of the medulla.

An NMDA agonist and/or partial agonist included in a composition administered according to the present invention preferably includes a pharmaceutically acceptable carrier in a formulation for administration to a subject. The term "pharmaceutically acceptable carrier" as used herein is intended to refer to a carrier or diluent that is generally non-toxic to an intended recipient and which does not significantly inhibit activity of an active agent included in the composition.

An NMDA agonist and/or partial agonist is administered to a subject by any of a variety of systemic and/or local routes illustratively including intravenous, oral, parenteral, intrathecal, intracerebroventricular, and mucosal. In a particular embodiment of a method of the present invention, an NMDA agonist and/or partial agonist is administered to a subject by local administration to neurons of the NTS, such as via a conduit having an outlet implanted in or near the NTS.

A therapeutically effective amount of an NMDA agonist and/or partial agonist is administered to a subject in an embodiment of the present invention. The term "therapeutically effective amount" as used herein is intended to mean an amount of an inventive composition which is effective to stimulate NOVA receptors of the NTS innervated by baroreceptor afferents, thereby sensitizing the NTS neurons. A therapeutically effective amount of an inventive composition will vary depending on the particular agonist or partial agonist administered, the severity of the condition, and the general physical characteristics of the individual to be treated. One of skill in the art could determine a therapeutically effective amount in view of these and other considerations typical in medical practice. In general it is contemplated that a therapeutically effective amount would be in the range of about 0.001 mg/kg-100 mg/kg body weight/day, more preferably in the range of about 0.01-10 mg/kg, and further preferably in the range of about 0.1-5 mg/kg. Exemplary human protocols for use of D-cycloserine are described in detail in Ressler K J, et al., Arch Gen Psychiatry, 61:1136-44, 2004. Detailed information concerning materials, equipment and processes for preparing and manufacturing various dosage forms may be found in Pharmaceutical Dosage Forms: Tablets, eds. H. A. Lieberman et al., New York: Marcel Dekker, Inc., 1989, and in L. V. Allen, Jr. et al., Ansel's Pharmaceutical Dosage Forms and Drug Delivery Systems, 8th Ed., Philadelphia, Pa.: Lippincott, Williams & Wilkins, 2004. Further examples and details of pharmacological formulations and ingredients are found in standard references such as: A. R. Gennaro, Remington: The Science and Practice of Pharmacy, Lippincott Williams & Wilkins, 20th ed. (2003); L. V. Allen, Jr. et al., Ansel's Pharmaceutical Dosage Forms and Drug Delivery Systems, 8th Ed. (Philadelphia, Pa.: Lippincott, Williams & Wilkins, 2004); J. G. Hardman et al., Goodman & Gilman's The Pharmacological Basis of Therapeutics, McGraw-Hill Professional, 10th ed. (2001).

In further embodiments, a method of regulating blood pressure in a subject includes measuring a physiological parameter indicative of a baseline state of the subject relating to blood pressure regulation. Such a measurement is termed a "baseline measurement." Optionally and preferably, the physiological parameter is measured two or more times and the measurements averaged to establish an "averaged baseline measurement."

A particular physiological parameter measured is blood pressure of the subject. In this regard, various intermittent and continuous, invasive and non-invasive blood pressure measuring techniques are known in the art. Measurement of blood pressure is achieved by any of various methods and devices known in the art. For instance, methods illustratively including auscultatory methods and oscillometric methods are used to measure blood pressure. Devices for measuring blood pressure illustratively include external devices such as sphygmomanometers and oscillometric monitors; and invasive devices such as an intravascular cannula connected to an electronic pressure transducer. Exemplary blood pressure measurement techniques are described in Staessen, J. A. et al., Hypertension., 26:912-918, 1995.

Alternative or additional physiological parameters indicative of a baseline state of the subject relating to blood pressure regulation include heart rate variability and blood pressure variability.

A test stimulus is administered to a component of an endogenous blood pressure regulation system of the subject. A physiological parameter is measured to assess the response of the endogenous blood pressure regulation system to the test stimulus relative to the baseline measurement. The difference between the measured baseline and the response to the test stimulus is termed the "test stimulus-induced response." Optionally and preferably, the physiological parameter is measured two or more times and the measurements averaged to establish an "averaged test stimulus-induced response." Thus, for example, blood pressure is measured following administration of a test stimulus to determine the extent of a change in blood pressure in response to the test stimulus. An exemplary test stimulus is a stimulus sufficient to stimulate an A fiber of an afferent baroreceptor nerve, such as the aortic depressor nerve and/or carotid sinus nerve, without substantially stimulating C fibers of the afferent baroreceptor nerve.

An induction stimulus is administered to a component of an endogenous blood pressure regulation system of the subject. The induction stimulus is a stimulus sufficient to sensitize a component of the endogenous blood pressure regulation system of the subject to a post-regulation-induction stimulus. Optionally, a physiological parameter is measured to assess the response of the endogenous blood pressure regulation system to the regulation-induction stimulus.

The effect of a "post-induction stimulus," also called a "second stimulus," on a component of an endogenous blood pressure regulation system of the subject is also optionally and preferably measured. The post-induction stimulus is substantially similar in strength to the test stimulus. A physiological parameter is measured to assess the response of the endogenous blood pressure regulation system to the post-induction stimulus relative to the baseline measurement. The difference between the measured baseline and the response to the test stimulus is termed the "post-induction stimulus response." Optionally and preferably, the physiological parameter is measured two or more times and the measurements averaged to establish an "averaged post-induction stimulus response."

In addition, a difference between the test stimulus-induced response and the post-induction stimulus response may be measured to demonstrate a therapeutic effect of a method according to the present invention since the post-induction stimulus response is greater than the test stimulus-induced response.

The test stimulus and the post-induction stimulus are each optionally exogenously administered, such as by use of an external, implanted or partially implanted electrode. Alternatively, either or both of the test stimulus and the post-regulation-induction stimulus may be endogenous stimuli. Thus, for example, an endogenous test stimulus and/or post-regulation-induction stimulus is a rise in blood pressure in the subject.

The second stimulus is "weaker" than an induction stimulus typically. Thus, for example, a tetanic electrical stimulus is administered as an induction stimulus and the second stimulus is a non-tetanic stimulus. The second stimulus is effective to regulate blood pressure in the subject.

Further embodiments of methods of regulating blood pressure according to the present invention include a) selecting stimulus parameters for administering a tetanic electrical stimulus to high threshold C-fibers of baroreceptor afferents, the stimulus parameters comprising a frequency in the range of about 50-150 Hz; a high current pulse intensity in the range of about 50-600 microAmps; a pulse duration in the range of about 100-500 microseconds; a train duration in the range of about 1-5 s, a train frequency in the range of about 1 train/ 10-20 s; and a train number in the range of about 5-20 trains; b) stimulating low threshold A-fibers of baroreceptor afferents in a subject, the stimulating comprising administering a stimulus pulse train of low current intensity characterized by stimulus parameters comprising a frequency in the range of about 15-60 Hz; current pulse intensity in the range of about 5-50 microAmps; a pulse duration in the range of about 100-500 microseconds; and a stimulation duration in the range of about 10-60 seconds; c) measuring evoked blood pressure (EBP) response in the subject to the stimulating low threshold A-fibers of baroreceptor afferents to determine a first average EBP response value; d) stimulating high threshold C-fibers of baroreceptor afferents using the stimulus parameters selected in a); e) measuring EBP response to the stimulating low threshold A-fibers of baroreceptor afferents to determine a second average EBP response value; f) comparing the first average EBP response value and the second average EBP response value, wherein successful induction of an enhanced baroreflex is indicated by the second average EBP response value greater than the first average EBP response value; g) repeating a)-f) until the second average EBP response value is greater than the first average EBP response value, indicative that selected stimulus parameters successfully inducing an enhanced baroreflex; and h) administering one or more additional induction stimuli characterized by the selected stimulus parameters successful induction of an enhanced baroreflex at about 10-15 hour intervals.

Embodiments of inventive compositions and methods are illustrated in the following examples. These examples are provided for illustrative purposes and are not considered limitations on the scope of inventive compositions and methods.

EXAMPLES

Example 1

An exemplary procedure for increasing the effectiveness of blood pressure regulation and thus, controlling hypertension is described in this example.

A brief tetanic baroreceptor electrical stimulation (pulse parameters: High Current, 300 μs, 100 Hz; 1 s/10 s, 10 trains) produces a long-term, 10-15 hours, blood pressure depression in one embodiment.

The following are included in an exemplary embodiment of an inventive method:

Step 1: Stimulate low threshold A-fibers of baroreceptors, with pulse trains (15-60 Hz; 100 μs; 10 s) of low current intensity (5-25 μA); and measure the evoked blood pressure (EBP) responses to each stimulus. Ensemble average at least 10 stimulations.

Step 2: Apply a tetanic electrical stimulus (>50 μA, 300 μs, 100 Hz; 1 s/10 s, 10 trains) to the same nerve paths to activate high threshold C-fibers, and thus to induce the LTP, also termed sensitization herein, increasing the gain of the baroreflex afferent path.

Step 3: Repeat Step 1, and compare the average EBP response from the Step 3 with that from the Step 1. If the average EBP of Step 3 is greater than that of Step 1, then the LTP has been successfully induced, that is, the NTS neurons have been sensitized, and these are the correct parameters for therapy; otherwise, repeat the Step 2 with an increasing current intensity until LTP is induced. The successful induction of LTP, that is, NTS neuron sensitization, is indicated by a larger EBP response, to a same A-fiber stimulation, subsequent to the LTP induction than that prior to the LTP induction.

The LTP effect should persist for at least about 10 hours, reducing both the blood pressure level, and blood pressure variability.

Example 2

Methods according to embodiments of the present invention are exemplified by studies using stimulation of the aortic depressor nerve, in a special chronic rat preparation. A short, 10 second tetanus, over a 100 second period, tetanic (high-frequency) stimulation increases the sensitivity of the baroreceptor fibers, and the heightened sensitivity of the aortic baroreceptor input to the NTS persists for 10-15 hours.

Experiments are conducted using adult Sprague-Dawley female rats, weighing

Rats, 225-275 g, are neuromuscular blocked (NM) with alpha-cobratoxin, and positive pressure ventilated at a rate of 72 breaths/min. Electrocardiogram, arterial blood pressure (ABP), and venous blood pressure are recorded; temperature is servo-regulated at 37° C. A Ta-Ta$_2$O$_5$ capacitance electrode is attached to the left ADN for nerve stimulation as described in detail in Dworkin, B. R., et al., 2000, Am J Physiol Regulatory Integrative Comp Physiol 270: R1910-R1921. With this electrode, the rat ADN can be stimulated thousands of times without damage. Stimulus patterns are generated and data are acquired and analyzed by Spike 2 (Cambridge Electronic Design Limited, Cambridge, UK). For ER recordings, a 1-2 MΩ glass insulated tungsten electrode (Alpha-Omega, Alpharetta, Ga.) is placed stereotaxically in the dmNTS, through the ventral membrane of the foramen magnum. NTS multi-neuron activity is sampled at 10 kHz.

Figure 4:
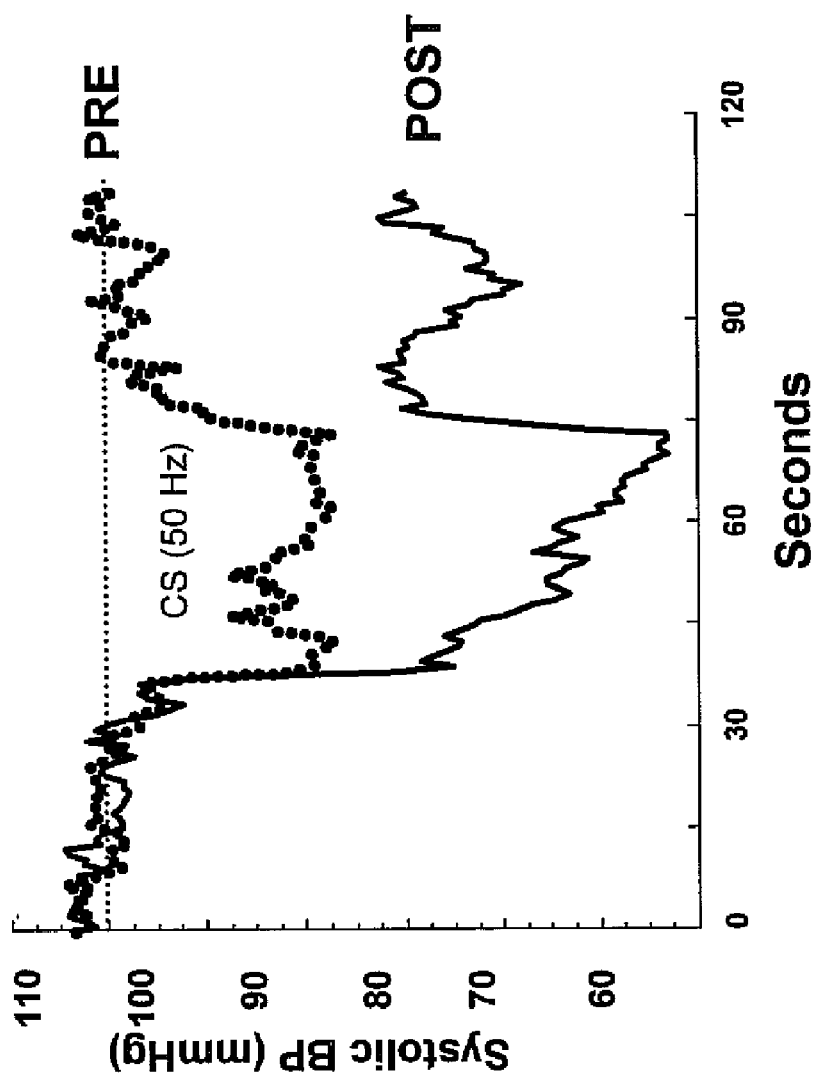
FIG. 4 is an image illustrating traces of systolic blood pressure before and after administration of an induction stimulus.

FIG. 4 shows data collected on a NUB rat treated by homotopic conditioning in which the conditioning stimulus was baroreceptor afferent A fiber stimulation at using pulse trains of 25 microamps, 100 microseconds and 50 impulses/s followed by an unconditioned stimulus, the induction stimulus, effective to stimulate baroreceptor afferent C fibers. The induction stimulus was characterized by pulse trains of 125 microamps, 200 microseconds and 5 impulses/s. Each alternate hour had 3 conditioning trials for a total of 54 trials in 36 hours. The "PRE" trace in FIG. 4 shows the time locked average systolic blood pressure response of 6 "test" trials immediately before conditioning. The "POST" trace shows the time locked average systolic blood pressure response of 6 trials immediately after the conditioning. Further details are described in J. P. Cacioppo, Handbook of Psychophysiology, Chapter 21, B. Dworkin, Interoception, Cambridge, 2007)

Figure 5:
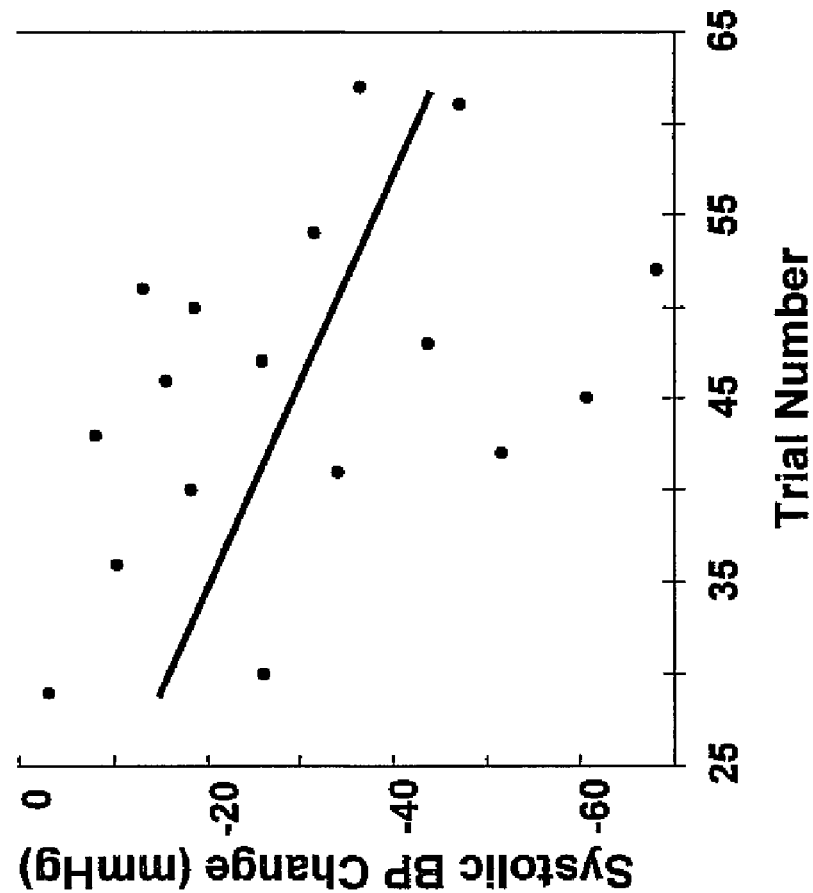
FIG. 5 is a graph showing a change in systolic blood pressure with homotopic conditioning of the baroreflex system.

FIG. 5 shows the magnitude of the blood pressure change to the conditioning stimulus during the 30 conditioning trials. The negative slope of the regression line, $r=-05.70$; $F=5.7$; $p<0.05$, indicates that the depressor response increased systematically with trials.

Figure 6:
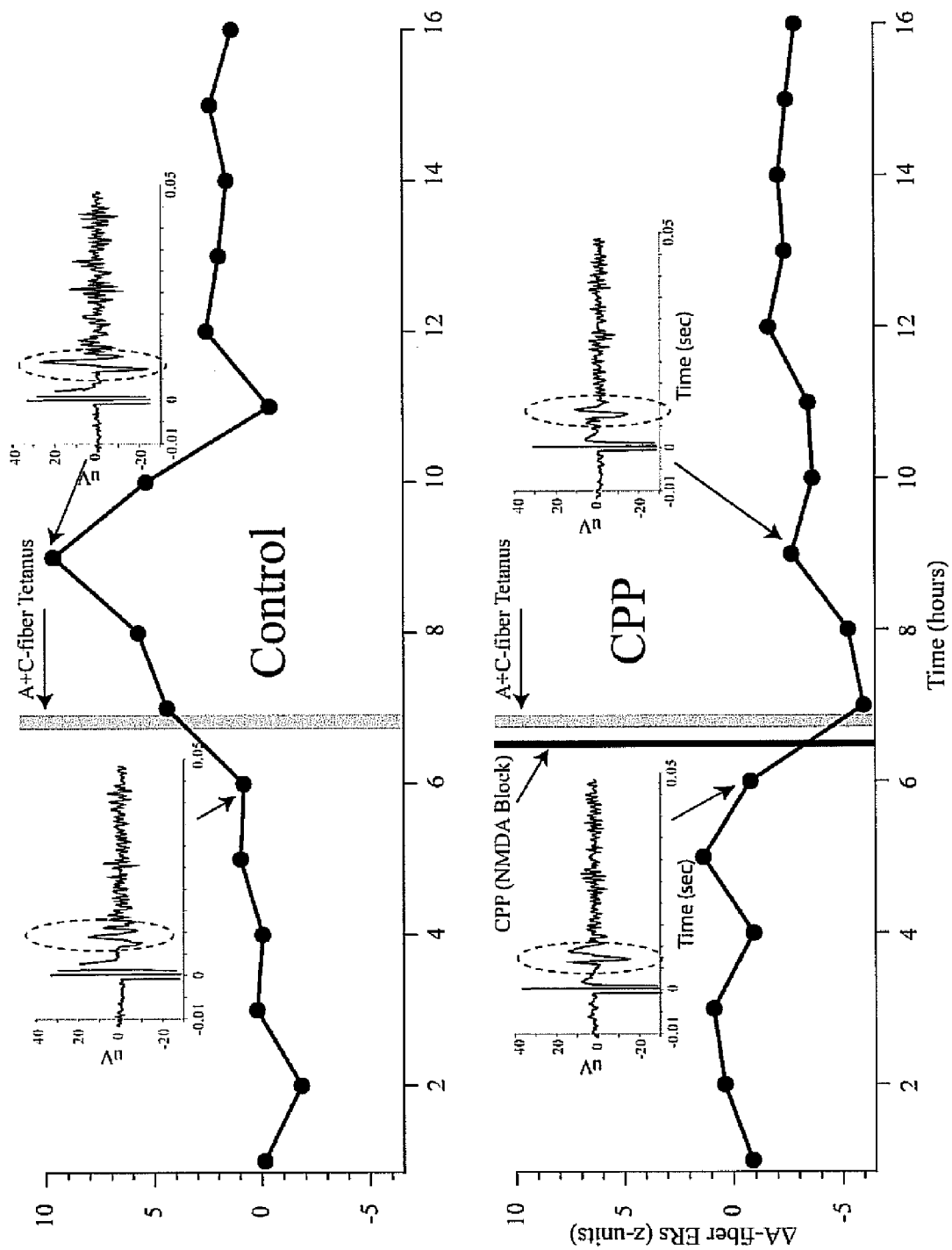
FIG. 6 shows two graphs and four inset traces of averaged evoked responses of nucleus tractus solitarius neurons to the ADN A-fiber stimulations for the hours indicated by the arrows before and after administration of an induction stimulus in the presence and absence of an NMDA receptor antagonist, CPP.

FIG. 6 illustrates the effect of an NMDA receptor antagonist on homotopic induction in the NTS. In this example, response of NTS neurons in a NMB rat to a test stimulus is measured before administration of an induction stimulus and after administration of an induction stimulus in the control, compared to before administration of an induction stimulus and after administration of an induction stimulus in the presence an NMDA antagonist 3-(2-carboxypiperazin-4-yl)-propyl-1-phosphoric acid (CPP). Parameters for the test stimuli: inter-pulse interval=6±1 s, 300 µs, and A-fiber only current intensity; parameters for the induction stimuli: 300 µs, 100 Hz, 1 s/10 s, 10 trains.

FIG. 6 illustrates that the NMDA receptor antagonist, 3-(2-Carboxypiperazin-4-yl)-propyl-1-phosphoric acid, CPP, blocked the effect of a A+C-fiber tetanus on the A-fiber ERs. The x-axis of the tope panel is identical to the x-axis of the lower panel. The vertical ordinate of the top panel is identical to the vertical ordinate of the lower panel. The vertical ordinate is in units of baseline standard deviation (z-units). Each point in the upper and lower panels is the hourly average magnitude of the A-fiber ERs.

The top panel of FIG. 6 shows a control experiment. For hours 1-6 of the control experiment A-fiber only baseline is shown, PW=300 µs, inter-pulse interval=6±1 s. The grey vertical bar indicates the time at which an A+C-fiber tetanus is administered. At post-tetanus times, hours 7-16, the ERs to A-fiber only stimulus pattern is shown.

The bottom panel illustrates results from an experiment in which CPP infusion precedes tetanus. For hours 1-6 of the control experiment A-fiber only baseline is shown, PW=300 µs, inter-pulse interval=6±1 s. The black vertical bar indicates CPP administration. CPP is administered in an amount of 2.5 mg total, administered as 1.25 mg/ml×0.2 ml/min×10 min, i.v. The grey vertical bar indicates the time at which an A+C-fiber tetanus is administered. At post-tetanus times, hours 7-16, the ERs to A-fiber only stimulus pattern is shown. The insets show the averaged ER traces, circled, for the hour indicated by the arrow. The CPP procedure was on day 7, and the Control followed on day 8 of a preparation, which was fully functional for 12 days. The x-axis and y-axis of each inset is identical to the labeled inset.

Any patents or publications mentioned in this specification are incorporated herein by reference to the same extent as if each individual publication is specifically and individually indicated to be incorporated by reference. U.S. Provisional Patent Application Ser. No. 60/824,519 filed Sep. 5, 2006 is incorporated herein by reference in its entirety. U.S. Provisional Patent Application Ser. No. 60/828,475 filed Oct. 6, 2006 is incorporated herein by reference in its entirety.

The invention described herein is presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method for regulating blood pressure in a subject, comprising:
administering a first tetanic electrical induction stimulus, the first tetanic electrical induction stimulus effective to sensitize brainstem baroreflex neurons of a subject for a period of time in the range of about 10-15 hours to produce an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration, wherein the induction stimulus has diminished effectiveness to sensitize brainstem baroreflex neurons of the subject in the presence of an NMDA receptor antagonist, thereby regulating blood pressure in the subject.

2. The method of claim 1, further comprising administering one or more additional induction stimuli effective to sensitize brainstem baroreflex neurons of a subject at about 10-15 hour intervals following administering the first induction stimulus.

3. The method of claim 2 wherein the one or more additional tetanic electrical induction stimuli is administered to the subject by a stimulation device at least partially implanted in the body of the subject.

4. The method of claim 1 wherein the first tetanic electrical induction stimulus is delivered to a baroreceptor afferent of the subject.

5. The method of claim 1 wherein the first induction stimulus is a tetanic electrical stimulus delivered to an aortic depressor nerve of the subject.

6. The method of claim 1 wherein the first induction stimulus is a tetanic electrical stimulus delivered to a carotid sinus nerve of the subject.

7. The method of claim 1 wherein the first induction stimulus is a tetanic electrical stimulus delivered to at least one carotid sinus and/or to the aortic arch.

8. The method of claim 1 wherein the first tetanic electrical induction stimulus is administered by a stimulation device external to the body of the subject.

9. The method of claim 1 wherein the first tetanic electrical induction stimulus is administered to the subject by a stimulation device at least partially implanted in the body of the subject.

10. The method of claim 1 wherein the first tetanic electrical induction stimulus is administered to the subject by a stimulation device completely implanted in the body of the subject.

11. The method of claim 1 wherein the first induction stimulus is a dose of an NMDA receptor agonist delivered to the nucleus tractus solitarius of the subject.

12. The method of claim 1 wherein the tetanic electrical induction stimulus is effective to stimulate baroreceptor afferent C-fibers.

13. The method of claim 1 wherein the first tetanic electrical induction stimulus is administered to the subject by a stimulation device external to the body of the subject.

14. The method of claim 1, wherein the first tetanic electrical induction stimulus is effective to decrease variability in blood pressure in the subject over a period of time in the range of about 10-15 hours following the stimulus.

15. The method of claim 14 wherein the variability is decreased by about 5-50% for a duration of about 10-15 hours following the induction stimulus.

16. A method for regulating blood pressure in a subject, comprising:
administering a first tetanic electrical induction stimulus to a baroreceptor afferent of the subject, wherein the first tetanic electrical induction stimulus is effective to sensitize brainstem baroreflex neurons of the subject for a period of time in the range of about 10-15 hours to produce an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration, wherein the first tetanic electrical induction stimulus has diminished effectiveness to sensitize brainstem baroreflex neurons of the subject in the presence of an NMDA receptor antagonist, thereby regulating blood pressure in the subject.

17. The method of claim 16, further comprising:
administering one or more additional tetanic stimuli effective to sensitize brainstem baroreflex neurons of a subject for a period of time in the range of about 10-15 hours to produce an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration.

18. A method of regulating blood pressure in a subject, comprising:
a) selecting stimulus parameters for administering a tetanic electrical stimulus to high threshold C-fibers of baroreceptor afferents, the stimulus parameters comprising a frequency in the range of about 50-150 Hz; a high current pulse intensity in the range of about 50-600 microAmps; a pulse duration in the range of about 100-500 microseconds; a train duration in the range of about 1-5 s, a train frequency in the range of about 1 train/10-20 s; and a train number in the range of about 5-20 trains;
b) stimulating low threshold A-fibers of baroreceptor afferents in a subject, the stimulating comprising administering a stimulus pulse train of low current intensity characterized by stimulus parameters comprising a frequency in the range of about 15-60 Hz; current pulse intensity in the range of about 5-50 microAmps; a pulse duration in the range of about 100-500 microseconds; and a stimulation duration in the range of about 10-60 seconds;
c) measuring evoked blood pressure (EBP) response in the subject to the stimulating low threshold A-fibers of baroreceptor afferents to determine a first average EBP response value;
d) stimulating high threshold C-fibers of baroreceptor afferents using the stimulus parameters selected in a);
e) measuring EBP response to the stimulating low threshold A fibers of baroreceptor afferents to determine a second average EBP response value;
f) comparing the first average EBP response value and the second average EBP response value, wherein successful induction of an enhanced baroreflex is indicated by the second average EBP response value greater than the first average EBP response value;
g) repeating a)-f) until the second average EBP response value is greater than the first average EBP response value, indicative that selected stimulus parameters successfully inducing an enhanced baroreflex; and
h) administering one or more additional induction stimuli characterized by the selected stimulus parameters successful induction of an enhanced baroreflex at about 10-15 hour intervals.

19. A method for regulating blood pressure in a subject, consisting essentially of:
administering a first induction stimulus effective to sensitize brainstem baroreflex neurons of a subject for a period of time in the range of about 10-15 hours to produce an enhanced baroreflex in the subject, wherein the enhanced baroreflex is characterized in that a threshold blood pressure for generating a depressor response is lower than prior to induction stimulus administration, the depressor response in the subject is larger than prior to induction stimulus administration or both the threshold blood pressure for generating a depressor response is lower than prior to induction stimulus administration and the depressor response in the subject is larger than prior to induction stimulus administration, wherein the induction stimulus has diminished effectiveness to sensitize brainstem baroreflex neurons of the subject in the presence of an NNIDA receptor antagonist; and
administering one or more additional induction stimuli at about 10-15 hour intervals following administering the first induction stimulus, the additional induction stimuli effective to sensitize brainstem baroreflex neurons of a subject, thereby regulating blood pressure in the subject.

* * * * *

UNITED STATES PATENT AND TRADEMARK OFFICE
CERTIFICATE OF CORRECTION

PATENT NO. : 8,175,712 B2  
APPLICATION NO. : 11/850251  
DATED : May 8, 2012  
INVENTOR(S) : Xiaorui Tang et al.

Page 1 of 1

It is certified that error appears in the above-identified patent and that said Letters Patent is hereby corrected as shown below:

In the Specification:

Column 8, line number 23, Delete "NTIS", Insert --NTS--.

Column 11, line number 61, Delete "NOVA", Insert --NMDA--.

Column 15, line number 13, Delete "NUB", Insert --NMB--.

In the Claims:

Column 18, claim 19, line number 60, Delete "NNIDA", Insert --NMDA--.

Signed and Sealed this  
Twenty-fourth Day of June, 2014

Michelle K. Lee  
*Deputy Director of the United States Patent and Trademark Office*